United States Patent
Steiger et al.

(10) Patent No.: US 8,580,989 B2
(45) Date of Patent: Nov. 12, 2013

(54) PROCESS FOR THE PREPARATION OF INDIUM CHLORDIALKOXIDES

(75) Inventors: Juergen Steiger, Duesseldorf (DE); Alexey Merkulov, Ludwigshafen (DE); Dennis Fruehling, Marl (DE); Arne Hoppe, Herne (DE); Nicole Brausch, Essen (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 13/515,007

(22) PCT Filed: Jul. 1, 2010

(86) PCT No.: PCT/EP2010/059376
§ 371 (c)(1),
(2), (4) Date: Jun. 11, 2012

(87) PCT Pub. No.: WO2011/072887
PCT Pub. Date: Jun. 23, 2011

(65) Prior Publication Data
US 2012/0289728 A1    Nov. 15, 2012

(30) Foreign Application Priority Data
Dec. 18, 2009   (DE) .......................... 10 2009 054 998

(51) Int. Cl.
*C07F 5/00*   (2006.01)
(52) U.S. Cl.
USPC ............................. 556/1; 438/99; 427/255.19
(58) Field of Classification Search
USPC ............................. 556/1; 427/255.19; 438/99
See application file for complete search history.

(56) References Cited

U.S. PATENT DOCUMENTS

| 4,681,959 A | 7/1987 | Ayen et al. |
| 2010/0132788 A1 | 6/2010 | Petrat et al. |
| 2011/0193084 A1 | 8/2011 | Thiem et al. |
| 2011/0309313 A1 | 12/2011 | Steiger et al. |
| 2011/0315982 A1 | 12/2011 | Hoppe et al. |
| 2012/0213980 A1 | 8/2012 | Arning et al. |

FOREIGN PATENT DOCUMENTS

| JP | 59 198606 | 11/1984 |
| JP | 59 198607 | 11/1984 |
| JP | 1 115010 | 5/1989 |
| JP | 2 113033 | 4/1990 |
| JP | 2 145459 | 6/1990 |

OTHER PUBLICATIONS

International Search Report Issued Oct. 15, 2010 in PCT/EP10/59376 filed Jul. 1, 2010.
U.S. Appl. No. 13/391,114, filed Apr. 27, 2012, Steiger, et al.
U.S. Appl. No. 13/390,840, filed Apr. 5, 2012, Steiger, et al.
U.S. Appl. No. 13/516,900, filed Jun. 18, 2012, Steiger, et al.
U.S. Appl. No. 13/809,322, filed Jan. 9, 2013, Steiger, et al.
U.S. Appl. No. 13/809,423, filed Jan. 10, 2013, Steiger, et al.
U.S. Appl. No. 13/884,495, filed May 9, 2013, Steiger, et al.

*Primary Examiner* — Porfirio Nazario Gonzalez
(74) *Attorney, Agent, or Firm* — Oblon, Spivak, McClelland, Maier & Neustadt, L.L.P.

(57) ABSTRACT

The present invention relates to a process for the preparation of indium(III) halodialkoxides of the generic formula $InX(OR)_2$ where X=F, Cl, Br, I and R=alkyl radical, alkoxyalkyl radical, in which a composition (A) comprising an indium trihalide $InX_3$, where X=F, Cl, Br and/or I, and at least one alcohol of the generic formula ROH, where R=alkyl radical, alkyloxyalkyl radical, is reacted with a composition (B) comprising at least one secondary amine of the generic formula $R'_2NH$, where R'=alkyl radical, to the indium(III) halodialkoxides which can be prepared by the process and to their use.

14 Claims, 1 Drawing Sheet

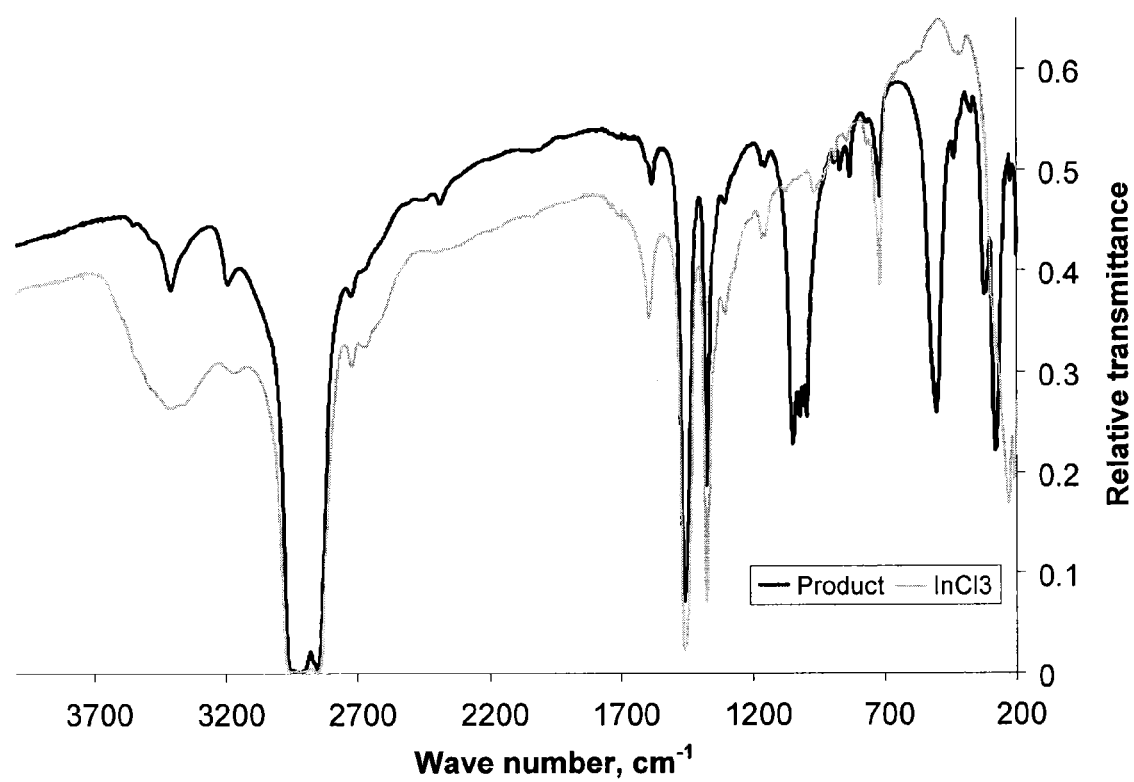

PROCESS FOR THE PREPARATION OF INDIUM CHLORDIALKOXIDES

The present invention relates to a process for the preparation of indium chlordialkoxides, the indium chlordialkoxides which can be prepared by the process according to the invention and the use thereof.

The production of semiconducting electronic component layers via printing and other liquid deposition processes permits far lower production costs in comparison with many other processes, for example, chemical vapour deposition (CVD), since the deposition of the semiconductor can be effected here in a continuous process. Moreover, in the case of relatively low process temperatures, there is the possibility of also working on flexible substrates and optionally (especially in the case of very thin layers and in particular in the case of oxidic semiconductors) of achieving an optical transparency of the printed layers. Here and below, semiconducting layers are to be understood as meaning layers which have charge carrier mobilities of from 1 to 50 $cm^2Ns$ in the case of a component having a channel length of 20 μm at 50 V gate source voltage and 50 V source drain voltage.

Since the material of the component layer to be produced via printing processes decisively determines the respective layer properties, its choice has a significant influence on each component containing this component layer. Important parameters for printed semiconductor layers are their respective charge carrier mobilities and processibilities and processing temperatures of the printable precursors used in their production. The materials should have good charge carrier mobility and be capable of being prepared from solution and at temperatures substantially below 500° C. in order to be suitable for a multiplicity of applications and substrates. Also desirable for many new applications is an optical transparency of the semiconducting layers produced.

Owing to the large energy gap from 3.6 to 3.75 eV (measured on layers applied by vapour deposition, H. S. Kim, P. D. Byrne, A. Facchetti, T. J. Marks; *J. Am. Chem. Soc.* 2008, 130, 12580-12581), indium oxide (indium(III) oxide, $In_2O_3$) is a promising and hence readily used semiconductor. Thin films of a few hundred nanometres thickness can moreover have a high transparency in the visible spectral range of greater than 90% at 550 nm. In extremely highly ordered single indium oxide crystals, charge carrier mobilities of up to 160 $cm^2Ns$ can also be measured. However, such values cannot yet be achieved to date by processing from solution (H. Nakazawa, Y. Ito, E. Matsumoto, K. Adachi, N. Aoki, Y. Ochiai; *J. Appl. Phys.* 2006, 100, 093706. and A. Gupta, H. Cao, Parekh, K. K. V. Rao, A. R. Raju, U. V. Waghmare; *J. Appl. Phys.* 2007, 101, 09N513).

Indium oxide is often used in particular together with tin (IV) oxide ($SnO_2$) as a semiconducting mixed oxide ITO Owing to the relatively high conductivity of ITO layers with simultaneous transparency in the visible spectral range, it is used, inter alia, in the area of liquid crystal display (LCD), in particular as a "thin-film electrode". These generally doped metal oxide layers are produced industrially in particular by expensive vapour deposition methods in a high vacuum. Owing to the great commercial interest in the ITO-coated substrates, there are now coating processes, especially based on sol-gel techniques, for indium oxide-containing layers.

In principle, there are two possibilities for the production of indium oxide semiconductors via a printing processes: 1) particle concepts in which (nano)particles are present in printable dispersion and are converted into the desired semiconductor layer after the printing process by sintering processes, and 2) precursor concepts in which at least one soluble or dispersible precursor is converted into an indium oxide-containing layer after the printing of a corresponding composition. The particle concept has two important advantages over the use of precursors: firstly, the particle dispersions have a colloidal instability which necessitates the use of dispersing additives (which are disadvantageous with respect to subsequent layer properties), and secondly many of the particles which can be used form only incomplete layers by sintering (for example owing to passivation layers), so that particulate structures may also occur in some cases in the layers. Considerable particle-particle resistance occurs at the particle boundary thereof and reduces the mobility of the charge carriers and increases the general layer resistance.

There are various precursors for the production of indium oxide layers. Thus, in addition to indium salts, it is possible to use indium alkoxides (homoleptic, compounds, i.e. compounds having only indium and alkoxide radicals) as precursors for the production of indium oxide-containing layers.

For example, Marks et al. describe components in whose production a precursor-containing composition comprising the salt $InCl_3$ and the base monoethanolamine (MEA) dissolved in methoxyethanol is used. After spin-coating of the composition, the corresponding indium oxide layer is produced by a thermal treatment at 400° C. (H. S. Kim, P. D. Byrne, A. Facchetti, T. J. Marks; *J. Am. Chem. Soc.* 2008, 130, 12580-12581 and supplemental information).

Compared with indium salt-containing compositions, indium alkoxide-containing compositions have the advantage that they can be converted into indium oxide-containing coatings at lower temperatures. Furthermore, it was assumed to date that halogen-containing precursors potentially have the disadvantage of leading to halogen-containing layers of lower quality. For this reason, attempts at layer formation with indium alkoxides were carried out in the past.

Indium alkoxides and their synthesis have been described since the seventies of the preceding centuries.

Thus, for example, Carmalt et al., in a review article, summarize the data known up to this time concerning synthesis, structure and reactivities of, inter alia, indium(III) alkoxides and alkylalkoxides (Carmalt et al., Coord. Chem Rev. 250 (2006), 682-709).

One of the longest known syntheses of indium alkoxides is described by Chatterjee et al. They describe the preparation of indium trisalkoxide $In(OR)_3$ from indium(III) chloride ($InCl_3$) with sodium alkoxide Na—OR, R representing-methyl, -ethyl, isopropyl, n-butyl, sec-butyl, tert-butyl and n-pentyl, sec-pentyl and tert-pentyl radicals (S. Chatterjee, S. R. Bindal, R. C. Mehrotra; *J. Indian Chem. Soc.* 1976, 53, 867).

Bradley et al. report a similar reaction to Chatterjee et al. and, with almost identical starting materials ($InCl_3$, isopropyl-sodium) and reaction conditions, obtain an indium-oxo cluster with oxygen as a central atom (D. C. Bradley, H. Chudzynska, D. M. Frigo, M. E. Hammond, M. B. Hursthouse, M. A. Mazid; *Polyhedron* 1990, 9, 719).

A particularly good variant of this process, which leads to particularly low contamination of chlorine in the product, is described in U.S. 2009-0112012 Aa. The efforts to achieve as low a degree as possible of chlorine impurities in the product are attributable to the fact that it was assumed to date that chlorine impurities contribute to reduction in the performance or the life time of electronic components (cf. for example U.S. Pat. No. 6,426,425 B2).

Also based on an indium halide, but on other bases, is the process described in U.S. Pat. No. 5,237,081 A for the preparation of pure indium alkoxides, in which an indium(III) halide is reacted in a basic medium with an alcohol. The base is said to be a strong base having low nucleophilicity. Bases mentioned by way of example are tertiary amines in addition to complex cyclic heterocycles mentioned by way of example.

U.S. Pat. No. 4,681,959 A describes a general two-stage process for the preparation of metal alkoxides (in particular tetraalkoxy compounds, such as tetramethyl titanate), in which a halide of an at least divalent metal is reacted with an alcohol, if desired in the presence of an aromatic solvent, initially to give an intermediate (a halogen-alkoxy compound of the metal). The intermediate is then reacted with an alcohol in the presence of a hydrogen halide acceptor (in particular a tertiary amine) with formation of the metal alkoxide.

Alternative synthesis routes to homoleptic indium alkoxide complexes are described by Seigi Suh et al. in J. Am. Chem. Soc. 2000, 122, 9396-9404. The processes described there are, however, very complicated and/or are based on starting materials which are not commercially available (and therefore first have to be synthesized in a disadvantageous manner in an upstream step).

Surprisingly, it has now been found that the assumption to date that chlorine-containing precursors inevitably lead to disadvantageous layers is not always true. Thus, a precursor-based process in which a liquid precursor composition is applied to a substrate and the coating film is first treated with UV radiation before thermal conversion results in even better layers in the case of the use of indium chlordialkoxides instead of indium alkoxides, since these have better electrical properties, in particular higher field effect mobilities $\mu_{FET}$. Thus, processes for synthesizing indium chlordialkoxides are of considerable interest.

A general process for the preparation of halogen-alkoxy-metal compounds is described in U.S. Pat. No. 4,681,959 A: this describes in general a two-stage process for the preparation of metal alkoxides (in particular tetraalkoxy compounds, such as tetramethyl titanate), in which a halide of an at least divalent metal is reacted with an alcohol—if desired in the presence of an aromatic solvent—initially to give an intermediate (halogen-alkoxy compound of metal). Hydrogen halide formed is preferably expelled with an inert gas such as, for example, nitrogen. However, the process described there has the disadvantage that, where indium halides are used as starting materials, the reaction with alcohol takes place very slowly or ends after the formation of adducts of the type $InCl_3(ROH)_x$.

Indium haloalkoxides and their synthesis are described in JP 02-113033 A and JP 02-145459 A. Thus, JP 02-113033 A discloses that chlorine-containing alkoxides of indium can be prepared, after dissolution of the indium chloride in an alcohol corresponding to the alkoxide radical to be incorporated, by subsequent addition of a certain proportion of an alkali metal or an alkali metal alkoxide. A corresponding process is also described in JP 02-145459 A. However, the possible contamination of the resulting indium chloralkoxide to sodium constitute a disadvantage of these processes.

It is therefore the object of the present invention to provide processes for synthesizing indium chlorodialkoxides which avoid the disadvantages of the prior art, in particular the slow reaction rates and the resulting impurities in the synthesis.

This object is surprisingly achieved by the process according to the invention for the preparation of indium(III) halodialkoxides of the generic formula $InX(OR)_2$ where X=F, Cl, Br, I and R=alkyl radical, alkyloxyalkyl radical, in which a composition (A) comprising an indium trihalide $InX_3$, where X=F, Cl, Br and/or I, and at least one alcohol of the generic formula ROH, where R=alkyl radical, oxyalkyl radical, is reacted with a composition (B) comprising at least one secondary amine of the generic formula $R'_2NH$, where R'=alkyl radical.

An alkyl or alkyloxyalkyl radical R is preferably to be understood as meaning a C1- to C15-alkyl or alkoxyalkyl group, i.e. an alkyl or alkyloxyalkyl group having altogether 1-15 carbon atoms. It is preferably an alkyl or alkyloxyalkyl radical R selected from —$CH_3$, —$CH_2CH_3$, —$CH_2CH_2OCH_3$, —$CH(CH_3)_2$ or —$C(CH_3)_3$.

In principle, all indium trihalides $InX_3$ may be used. In these, X, in each case independently of one another, may be F, Cl, Br and/or I. However, indium trihalides of only one halide, i.e. the indium trihalides $InF_3$, $InCl_3$, $InBr_3$, or $InI_3$, are preferably used. Owing to their ready availability, the use of the indium trihalides $InCl_3$ and $InBr_3$ is particularly preferred.

The indium trihalide $InX_3$ is preferably used in proportions from 0.1 to 50% by weight, particularly preferably 1 to 25% by weight, very particularly preferably 2 to 10% by weight, based on the total mass of the composition (A).

The composition (A) comprising the indium trihalide may comprise it in dissolved form i.e. in dissociated form or at the molecular level complexed with solvent molecules/alcohol molecules, or dispersed in the liquid phase.

The composition (A) furthermore has at least one alcohol of the generic formula ROH, where R=alkyl or alkoxyalkyl radical. Thus, the composition may also have two or more alcohols. For the preferred production of indium(III) halodialkoxides of a specific type of alkoxides, however, only one alcohol should be present in the composition (A).

Alcohols which can preferably be used have radicals R selected from C1- to C15-alkyl or alkoxyalkyl radicals, i.e. alkyl or alkyloxyalkyl groups having altogether 1-15 carbon atoms. Alcohols having an alkyl or alkyloxyalkyl radical R selected from —$CH_3$, —$CH_2CH_3$, —$CH_2CH_2OCH_3$, —$CH(CH_3)_2$ or —$C(CH_3)_3$ are preferably used.

The alcohol ROH is preferably used in proportions from 50 to 99.9% by weight, particularly preferably 75 to 99% by weight, very particularly preferably 80 to 96% by weight, based on the total mass of the composition (A).

The composition (A) may furthermore have at least one liquid solvent or a dispersing medium which is inert with respect to the reaction i.e. a solvent/dispersing medium or a mixture of different solvents/dispersing media which do not react with $InX_3$ under the reaction conditions. Aprotic solvents, in particular those selected from the group consisting of the aprotic nonpolar solvents, i.e. the alkanes, substituted alkanes, alkenes, alkynes, aromatics with or without aliphatic or aromatic substituents, halogenated hydrocarbons and tetramethylsilane, and from the group consisting of the aprotic polar solvents, i.e. the ethers, aromatic ethers, substituted ethers, esters or acid anhydrides, ketones, tertiary amines, nitromethane, DMF (dimethylformamide), DMSO (dimethyl sulfoxide) or propylene carbonate, can preferably be used.

If at least one such liquid solvent or dispersing medium which is inert with respect to the reaction is present in the composition (A), its proportion, based on the composition, is preferably 1 to 50% by weight, particularly preferably 1 to 25% by weight, very particularly preferably 1 to 10% by weight, based on the total mass of the composition.

According to the invention, the composition (A) comprising $InX_3$ is furthermore reacted with a composition (B) comprising at least one secondary amine of the generic formula $R'_2NH$, where R'=alkyl radical, for the synthesis of the indium(III) halodialkoxides. The at least one secondary amine of the generic formula $R'_2NH$ is preferably a secondary amine having radicals R' independently of one another selected from the group consisting of $C_1$-$C_{10}$-alkyl radicals.

Preferably, only one secondary amine is used. More preferably, the secondary amine has the same alkyl radical as radicals R'. Particularly preferred radicals R' are linear $C_1$-$C_{10}$-alkyl radicals. Particularly good results are obtained with radicals R'=methyl, ethyl and n-propyl. Very particularly good results are obtained if a secondary amine of the generic formula R'$_2$NH, where R=methyl, is used, since this is particularly readily soluble in the preferably used solvents or dispersing media and therefore leads to particularly good yields.

For achieving particularly good yields, the at least one secondary amine is added in substantially at least twice the stochiometric amount relative to the indium trihalide $InX_3$. Particularly preferably, the secondary amine is used in an amount which corresponds to 4 to 6 times the molar amount of $InX_3$.

For achieving increased product yields, the secondary amine can be used not only in solution but preferably dispersed in a dispersing medium. The composition (B) can, however, comprise exclusively the secondary amine for a particularly simple reaction procedure.

The reaction is preferably carried out at a temperature in the range of 25° C.-250° C. The reaction is particularly preferably used at a temperature in the range from 25° C. to the temperature which corresponds to the boiling point of the alcohol used. Thus, the temperature is particularly preferably in the range from 25° C. to 125° C.

The synthesis can in principle be effected at atmospheric pressure or at increased pressure. However, the synthesis is preferably carried out at atmospheric pressure (1013 mbar).

The synthesis is furthermore preferably effected under anhydrous conditions, i.e. in the presence of not more than 200 ppm of $H_2O$. For achieving particularly good yields, the reaction should furthermore be carried out in an inert gas atmosphere, preferably in an Ar, He or $N_2$ atmosphere, particularly preferably in an $N_2$ atmosphere.

For achieving particularly high yields, the reaction mixture is furthermore cooled to a temperature in the range of 10-20° C. before working up.

The purification can preferably be effected by evaporating down the reaction mixture, taking up the residue in the alcohol used, filtering and washing. The product can then preferably be dried in a high vacuum.

The invention furthermore relates to the indium(III) halodialkoxides which can be prepared via the process according to the invention. These have the empirical formula $InX(OR)_2$ but may furthermore be coordinated or solvated in the crystal or in the aqueous phase with alcohol ROH coordinated from the synthesis or in secondary amine R'$_2$NH.

The indium(III) halodialkoxides which can be prepared by the process according to the invention are advantageously suitable for the production of indium oxide-containing coatings, in particular via wet chemical methods. In this case, indium oxide-containing coatings are to be understood as meaning both indium oxide layers and layers substantially comprising indium oxide and further metals and/or metal oxides. In the context of the present invention, an indium oxide layer is to be understood as meaning a metal-containing layer which can be produced from the indium alkoxides mentioned and has substantially indium atoms or ions, the indium atoms or ions substantially being present in oxide form. If desired, the indium oxide layer may also have halogen, carbene or alkoxide moieties from an incomplete conversion. The same also applies to layers substantially comprising indium oxide and further metals and/or metal oxides, with the proviso that these furthermore have the further metals and/or metal oxides.

The indium(III) halodialkoxides which can be prepared by the process according to the invention furthermore have the surprising advantage that they can be particularly readily used for the production of semiconducting indium oxide-containing coatings. The indium(III) halodialkoxides which can be prepared via the process according to the invention are to this extent furthermore advantageously suitable for the production of semiconducting or conducting layers for electronic components, in particular for the production of (thin-film) transistors, diodes or solar cells.

The following example is intended to explain the subject matter of the present invention further without itself having a limiting effect.

EXAMPLE

In a 500 ml round-bottomed glass flask freed from residual moisture, 5.0 g of indium(III) chloride ($InCl_3$, 22.5 mmol) are dissolved in 250 ml of dried methanol under an inert gas atmosphere by stirring, a residue of <10% by weight (based on the weight taken) of $InCl_3$ remaining behind. The metering of the base dimethylamine (5.0 g, corresponding to 111 mmol) is ensured via a mass flow controller and added in the stoichiometric amount, based on $InCl_3$, at room temperature over a period of five hours, a slightly exothermic reaction having been observed at the beginning. Thereafter, the solution is completely evaporated, and the remaining solid is taken up with 250 ml of dried methanol, filtered under inert gas $N_2$, washed several times (>10 processes) with dried methanol and dried in vacuo (<10 mbar) for 12 h at room temperature. The product yield was >80 mol % of indium(III) chlordimethoxide (indium content determined via ICP-OES, chlorine content determined argentometrically, content of carbon and hydrogen determined via combustion analysis). FIG. 1 shows an IR spectrum of the product and of the starting material $InCl_3$ used.

The invention claimed is:

1. A process for preparing an indium(III) halodialkoxide, the process comprising:
    reacting a composition (A) with a composition (B) to obtain the indium (III) halodialkoxide,
    wherein the indium (III) halodialkoxide is of formula:

each X is independently F, Cl, Br, or I,
    R is an alkyl radical or an alkyloxyalkyl radical, the composition (A) comprises an indium trihalide of formula $InX_3$ and an alcohol of formula ROH,
    the composition (B) comprises a secondary amine of formula R'$_2$NH, and
    R' is an alkyl radical.

2. The process of claim 1, wherein the indium trihalide is selected from the group consisting of $InF_3$, $InCl_3$, $InBr_3$, and $InI_3$.

3. The process of claim 1, wherein a proportion of the indium trihalide is from 0.1 to 50% by weight, based on a total mass of the composition (A).

4. The process of claim 1, wherein R in the alcohol is a $C_1$- to $C_{15}$-alkyl radical or a $C_1$- to $C_{15}$-alkoxyalkyl radical.

5. The process of claim 1, wherein a proportion of the alcohol is from 50 to 99.9% by weight, based on a total mass of the composition (A).

6. The process of claim 1, wherein the composition (A) further comprises a liquid solvent or a dispersing medium which is inert with respect to the reacting.

7. The process of claim 1, wherein each R' is a $C_1$-$C_{10}$-alkyl.

8. The process of claim 1, wherein a stoichiometric amount of the secondary amine is at least twice a stoichiometric amount of the indium trihalide.

9. A process for producing an indium oxide-containing coating, the process comprising preparing an indium (III) halodialkoxide according to the process of claim 1;
applying a composition comprising said indium (III) halodialkoxide to a substrate to form a coating film;
treating said coating film with UV radiation; and
thermally converting said coating film to produce an indium oxide-containing coating.

10. The process of claim 1, wherein the composition (A) comprises only one alcohol.

11. The process of claim 1, wherein each R is independently selected from the group consisting of —$CH_3$, —$CH_2CH_3$, —$CH_2CH_2OCH_3$, —$CH(CH_3)_2$ and —$C(CH_3)_3$.

12. The process of claim 5, wherein the proportion of the alcohol is from 75% to 99% by weight.

13. The process of claim 6, wherein the liquid solvent or dispersing medium comprises an aprotic solvent.

14. The process of claim 1, wherein a temperature of the reacting is from 25 to 250° C.

\* \* \* \* \*